(12) United States Patent
Schultz

(10) Patent No.: US 7,914,754 B2
(45) Date of Patent: Mar. 29, 2011

(54) INTEGRATED PRODUCTION OF FCC-PRODUCED C2 AND ETHYL BENZENE

(75) Inventor: Michael A. Schultz, Kuala Lumpur (MY)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/846,383

(22) Filed: Jul. 29, 2010

(65) Prior Publication Data

US 2010/0310431 A1   Dec. 9, 2010

Related U.S. Application Data

(62) Division of application No. 11/924,809, filed on Oct. 26, 2007, now Pat. No. 7,795,485.

(51) Int. Cl.
*B01J 8/18* (2006.01)
*C07C 2/66* (2006.01)

(52) U.S. Cl. ........ 422/620; 422/129; 422/139; 422/600; 422/608; 422/609; 422/621; 422/622; 585/448; 585/450; 585/709; 585/719; 585/910

(58) Field of Classification Search .................. 422/129, 422/139, 188, 190; 585/448, 450, 709, 719, 585/910
See application file for complete search history.

(56) References Cited

U.S. PATENT DOCUMENTS

| | | | | | |
|---|---|---|---|---|---|
| 2,439,080 | A | * | 4/1948 | Davies | 585/448 |
| 3,215,745 | A | * | 11/1965 | Frank | 568/572 |
| 3,639,497 | A | * | 2/1972 | Martel et al. | 585/804 |
| 3,950,448 | A | * | 4/1976 | Witt | 585/449 |
| 4,225,740 | A | * | 9/1980 | Chapman et al. | 585/719 |
| 4,225,741 | A | * | 9/1980 | Chapman et al. | 585/719 |
| 4,249,030 | A | * | 2/1981 | Chapman et al. | 585/716 |
| 5,856,607 | A | * | 1/1999 | Kim | 585/448 |
| 2001/0044565 | A1 | * | 11/2001 | Keady et al. | 585/809 |

* cited by examiner

*Primary Examiner* — Walter D Griffin
*Assistant Examiner* — Huy-Tram Nguyen
(74) *Attorney, Agent, or Firm* — David J Piasecki

(57) ABSTRACT

Processing schemes and arrangements are provided for obtaining ethylene and ethane via the catalytic cracking of a heavy hydrocarbon feedstock and converting the ethylene into ethyl benzene without separating the ethane from the feed stream. The disclosed processing schemes and arrangements advantageously eliminate any separation of ethylene from ethane produced by a FCC process prior to using the combined ethylene/ethane stream as a feed for an ethyl benzene process. Further, heat from the alkylation reactor is used for one of the strippers of the FCC process and at least one bottoms stream from alkylation process is used as an absorption solvent in the FCC process.

3 Claims, 3 Drawing Sheets

INTEGRATED PRODUCTION OF FCC-PRODUCED C2 AND ETHYL BENZENE

CROSS-REFERENCE TO RELATED APPLICATION

This application is a Division of prior U.S. application Ser. No. 11/924,809, which is filed Oct. 26, 2007 and is now U.S. Pat. No. 7,795,485, the contents of which are incorporated herein by reference thereto.

TECHNICAL FIELD

This disclosure relates generally to hydrocarbon processing. More specifically, this disclosure relates to the initial processing of hydrocarbon-containing materials into an intermediate stream of ethane and ethylene, produced by the cracking of a heavy hydrocarbon feedstock. This disclosure also relates to the subsequent use of said intermediate stream in the making of valuable aromatics, such as ethyl benzene.

BACKGROUND OF THE RELATED ART

Light olefins serve as feed materials for the production of numerous chemicals. Light olefins have traditionally been produced through the processes of steam or catalytic cracking of hydrocarbons derived from petroleum sources. Fluidized catalytic cracking (FCC) of heavy hydrocarbon streams is commonly carried out by contacting relatively high boiling hydrocarbons with a catalyst composed of finely divided or particulate solid material. The catalyst is transported in a fluid-like manner by transmitting a gas or vapor through the catalyst at sufficient velocity to produce a desired regime of fluid transport. Contact of the oil with the fluidized catalyst results in the cracking reaction.

FCC processing is more fully described in U.S. Pat. Nos. 5,360,533, 5,584,985, 5,858,206 and 6,843,906. Specific details of the various contact zones, regeneration zones, and stripping zones along with arrangements for conveying the catalyst between the various zones are well known to those skilled in the art.

The FCC reactor serves to crack gas oil or heavier feeds into a broad range of products. Cracked vapors from an FCC unit enter a separation zone, typically in the form of a main column, that provides a gas stream, a gasoline cut, light cycle oil (LCO) and clarified oil (CO) which includes heavy cycle oil (HCO) components. The gas stream may include hydrogen and $C_1$ and $C_2$ hydrocarbons, and liquefied petroleum gas ("LPG"), i.e., $C_3$ and $C_4$ hydrocarbons.

There is an increasing need for light olefins such as ethylene for the production of polyethylene, ethyl benzene and the like as opposed to heavier olefins. Research efforts have led to the development of an FCC process that produces or results in greater relative yields of light olefins, e.g., ethylene. Such processing is more fully described in U.S. Pat. No. 6,538,169.

Ethyl benzene is an important intermediate compound for the production of styrene. Although often present in small amounts in crude oil, ethyl benzene is produced in bulk quantities by combining the petrochemicals benzene and ethylene in an acid or zeolite catalyzed chemical reaction. Catalytic dehydrogenation of the ethyl benzene then gives hydrogen gas and styrene.

A conventional FCC process produces a combined ethylene/ethane stream. The ethylene/ethane stream is typically run through a splitter or distillation column to separate the ethylene from the ethane. The operation of such a splitter is energy intensive in addition to construction and maintenance costs.

In view of the increasing need and demand for light olefins such as ethylene and the use thereof in producing ethyl benzene, there is a need and a demand for improved processing and arrangements for the separation and recovery of light olefins, such as ethylene, from such FCC process effluent and the efficient conversion of those olefins into useful aromatic intermediates, such as ethyl benzene.

SUMMARY OF THE INVENTION

An integrated process is disclosed for (i) catalytically cracking (FCC) a heavy hydrocarbon feedstock, (ii) obtaining a combined ethylene/ethane stream, and (iii) reacting the ethylene of the combined ethane/ethylene stream with benzene to produce an ethyl benzene product stream. The integrated process comprises contacting a heavy hydrocarbon feedstock with a hydrocarbon cracking catalyst in a fluidized reaction zone to produce a hydrocarbon effluent stream that includes ethane and ethylene. The process then further comprises separating the combined ethane/ethylene stream from the hydrocarbon effluent stream, passing the combined ethane/ethylene stream to an alkylation reactor, and reacting at least some of the ethylene of the combined ethane/ethylene stream with benzene in the alkylation reactor to produce ethyl benzene.

By linking the FCC process directly to the ethyl benzene alkylation process, substantial capital and energy costs savings are achieved. First, the need for an ethylene/ethane splitter column is eliminated as ethane is inert to the ethyl benzene alkylation process and does not hinder the process in an appreciable way. Second, along with the energy savings achieved by eliminating the ethylene/ethane splitter, additional energy savings are achieved by linking the intercoolers used to cool the alkylation reactor to one of the splitter columns of the FCC process. Further, additional savings may achieved by using the bottoms stream from the ethyl benzene column of the alkylation zone in one of two ways. First the EB column bottoms may be used as a solvent in the primary absorber of the absorption zone, thereby reducing the dependence upon debutanized gasoline recycle as a solvent for the primary absorber. Second, the EB column bottoms may be used as a co-feed with the effluent stream to the main column of the separation zone. Employing either of these strategies can reduce the debutanized gasoline recycle demand by 5 to 10%.

The ethane is preferably not stripped from the combined ethane/ethylene stream prior to the combined ethane/ethylene stream entering the alkylation reactor. The ethane content of the combined ethane/ethylene stream may be up to or about 30 wt %.

Further, the combined ethane/ethylene stream entering the alkylation reactor is cold as it preferably has just passed through a demethanizer. The combined ethane/ethylene stream has a temperature of less than 0° C. (32° F.) which further reduces the duty of the intercoolers used to cool the alkylation reactor.

The alkylation reactor preferably includes six catalyst beds, six feed inlets, and two intercoolers disposed between the second and fourth catalyst beds.

As noted above, the hydrocarbon effluent generated in the FCC process passes through a separation zone to form a separator liquid stream and a separator vapor stream. $C_2-$ hydrocarbon materials are stripped from the separator liquid stream in a stripper column to form a $C_3+$ hydrocarbon process stream substantially free of $C_2-$ hydrocarbons. This stripper column may be advantageously heated with heat generated in the alkylation reactor. Thus, heat may be transferred from the intercoolers used to cool the alkylation reactor to the stripper column to lessen the cooling duty of the intercoolers.

Further, in generating the ethane/ethylene combined stream, the separator vapor stream is contacted with an absorption solvent in an absorption zone to remove $C_3+$ hydrocarbons therefrom to form the combined ethane/ethylene stream. More specifically, the separator vapor stream is contacted with the first absorption solvent comprising debutanized gasoline recycle in a primary absorber to form a first primary absorber process stream comprising ethane and ethylene and residual amounts of $C_3+$ hydrocarbons. In one embodiment, the first absorption solvent used in the primary absorber also comprises a bottoms stream from an ethyl benzene (EB) column of the ethyl benzene process. Employing this option eliminates the need for a transalkylation section as well as a polyethyl benzenes (PEB) column in the alkylation process. The EB bottoms stream supplements some of the debutanized gasoline recycle that is also used as the solvent in the primary absorber, thereby reducing the amount of recycle that is required. Any diethyl benzene (DEB) and polyethyl benzene (PEB) would ultimately end up as a high octane component in the gasoline product of the FCC process.

Another alternative is to send the EB column bottoms to the FCC main separation zone column, where the heavier species would be removed in a heavier fraction such as the heavy naphtha draw. The lighter species in this stream would still act to reduce the required debutanized gasoline recycle for use as the primary absorber solvent and will exit in the unstabilized gasoline that is recovered from the main column overhead.

Treatments to remove carbon dioxide, hydrogen sulfide, acetylene and methane from the combined ethane/ethylene stream may be carried out prior to passing of the ethane/ethylene stream to the alkylation reactor.

An integrated system for (i) catalytically cracking a hydrocarbon feedstock, (ii) obtaining selected hydrocarbon fractions including a combined ethane/ethylene stream and (iii) reacting the ethylene of the combined ethane/ethylene stream with benzene to produce an ethyl benzene product stream is provided. The integrated system includes a fluidized reactor zone wherein the hydrocarbon feedstock contacts a catalyst to produce a cracked effluent stream including ethane and ethylene. The system also includes a separation zone for separating the cracked effluent stream into at least one separator liquid stream and a separator vapor stream. The at least one separator liquid stream includes $C_3+$ hydrocarbons; the separator vapor stream includes ethane and ethylene. The system also includes an absorption zone to absorb $C_3+$ hydrocarbons from the separator vapor stream to form an absorption zone effluent stream comprising ethane and ethylene and a treatment zone to remove impurities other than ethane and ethylene from the absorption zone effluent stream to provide a combined ethane/ethylene stream. The combined ethane/ethylene stream is fed through a process line to an alkylation reactor for reacting at least some of the ethylene in the combined ethane/ethylene stream with benzene to form ethyl benzene.

Intercoolers used to cool the alkylation reactor can be used to drive one or more reboilers of a splitter column. The bottoms stream from an ethyl benzene column can be used as an absorber solvent or can be added to the cracked effluent stream.

Other advantages will be apparent to those skilled in the art from the following detailed description taken in conjunction with the appended claims and drawings.

DETAILED DESCRIPTION OF THE PRESENTLY PREFERRED EMBODIMENTS

Figure 1:
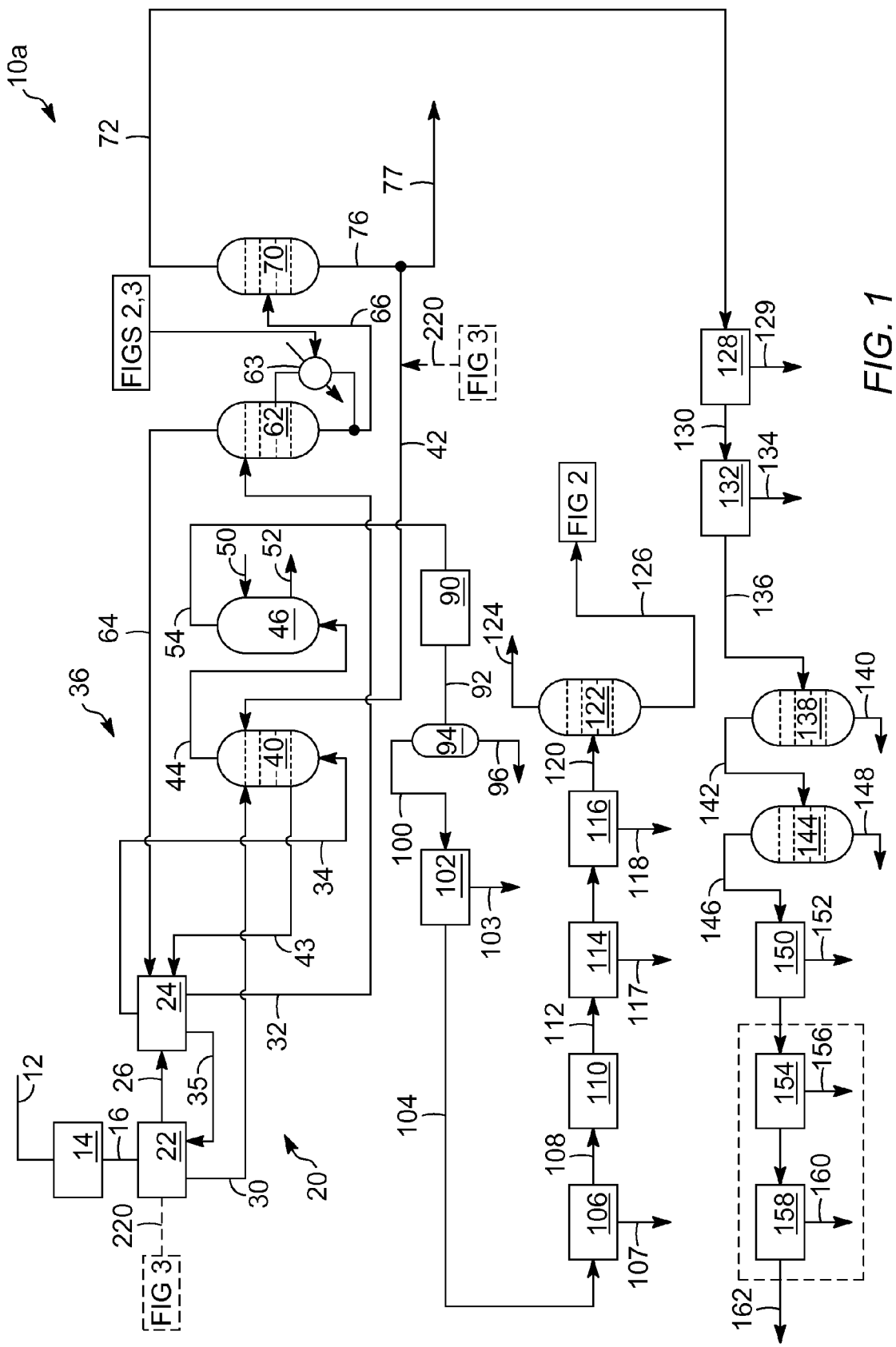
FIG. 1 is a simplified schematic diagram of a system for catalytic cracking a heavy hydrocarbon feedstock and obtaining selected hydrocarbon fractions, including C2 light olefins via an absorption-based product recovery.
Figure 2:
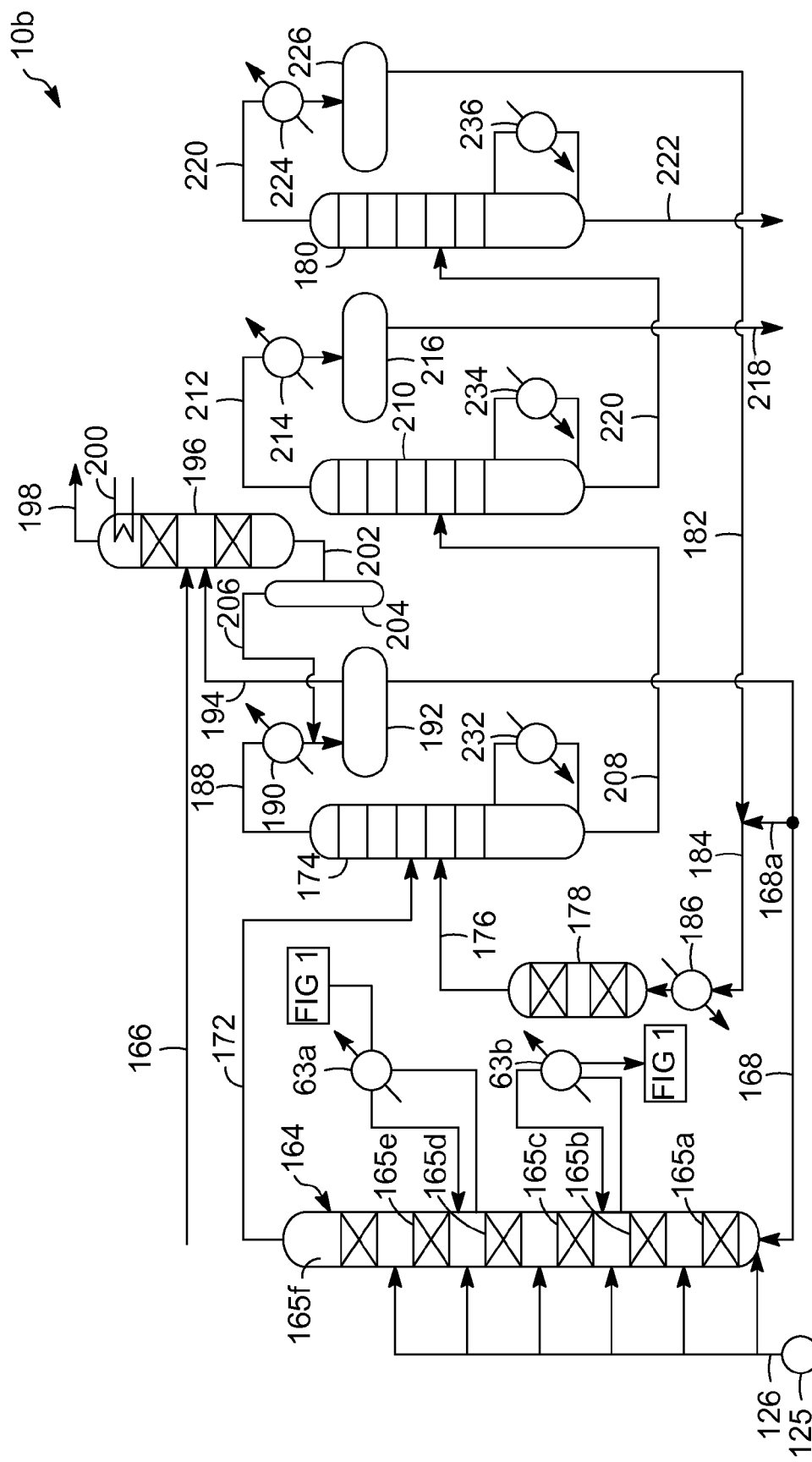
FIG. 2 is a simplified schematic diagram of a system for converting ethylene and benzene to ethyl benzene that is integrated with the system of FIG. 1.
Figure 3:
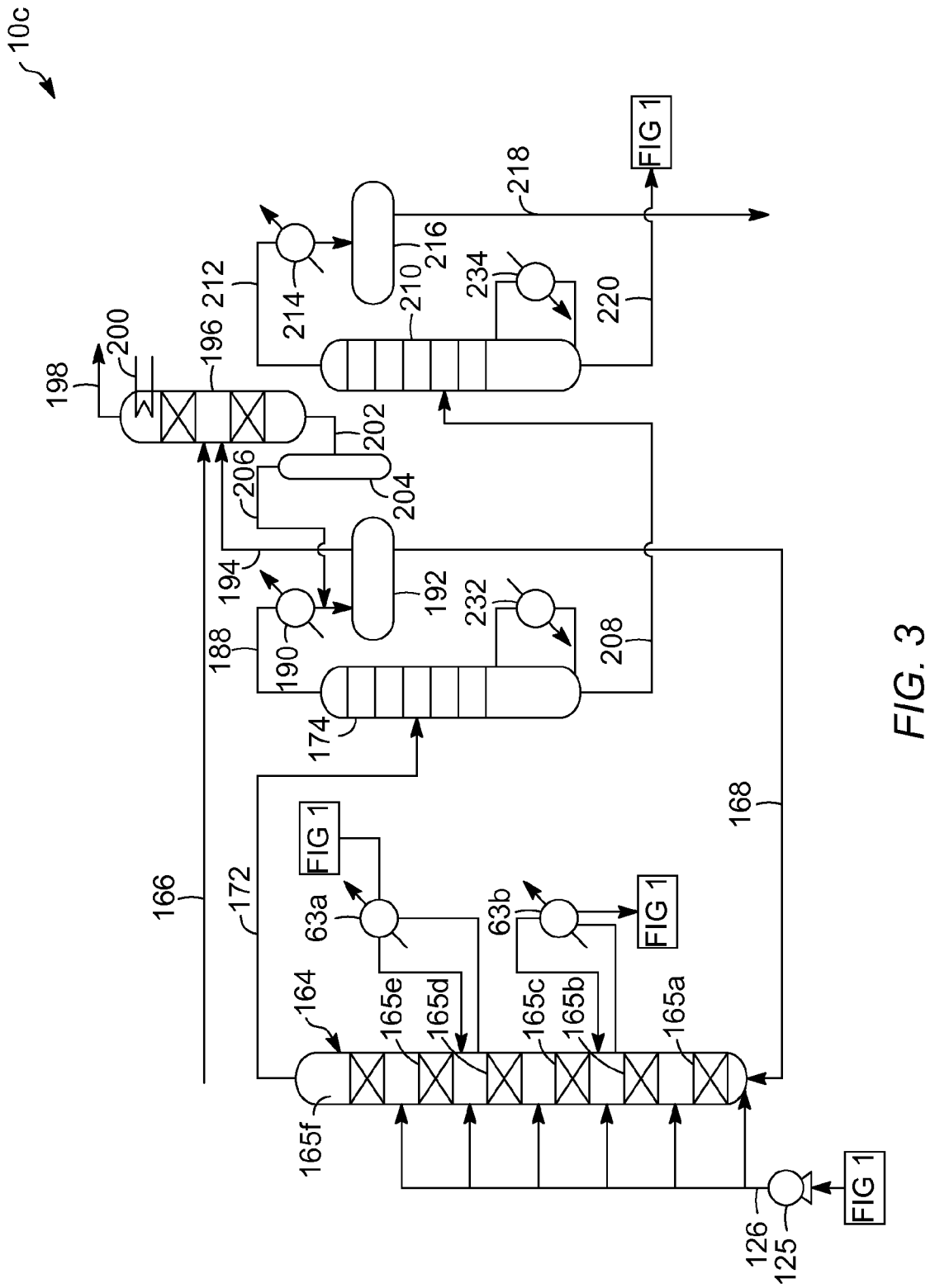
FIG. 3 is a simplified schematic diagram of another system for converting ethylene and benzene to ethyl benzene that is also integrated with the system of FIG. 1.

FIG. 1 schematically illustrates a system 10*a* for catalytic cracking a heavy hydrocarbon feedstock and obtaining light olefins via absorption-based product recovery and FIGS. 2 and 3 schematically illustrate systems 10*b*, 10*c* for efficiently converting the light olefins from the system 10*a* into one or more useful intermediates. Those skilled in the art and guided by the teachings herein provided will recognize and appreciate that the illustrated systems 10*a*, 10*b*, 10*c* have been simplified by eliminating some usual or customary pieces of process equipment including some heat exchangers, process control systems, pumps, fractionation systems, and the like. It may also be discerned that the process flows depicted in FIGS. 1-3 may be modified in many aspects without departing from the basic overall concepts disclosed herein.

In the cracking system 10*a*, a suitable heavy hydrocarbon feedstock stream is introduced via a line 12 into a fluidized reactor zone 14 wherein the heavy hydrocarbon feedstock contacts a hydrocarbon cracking catalyst zone to produce a hydrocarbon effluent comprising a range of hydrocarbon products, including light olefins such as ethylene and light hydrocarbons such as ethane.

Suitable fluidized catalytic cracking reactor zones for use in the practice of such an embodiment may, as is described in above-identified U.S. Pat. No. 6,538,169, include a separator vessel, a regenerator, a blending vessel, and a vertical riser that provides a pneumatic conveyance zone in which conversion takes place. The arrangement circulates catalyst and contacts the catalyst with the feed.

More specifically and as described therein, the FCC catalyst typically comprises two components that may or may not be on the same matrix. The two components are circulated throughout the reactor 14. The first component may include any of the well-known catalysts that are used in the art of fluidized catalytic cracking, such as an active amorphous clay-type catalyst and/or a high activity, crystalline molecular sieve. Molecular sieve catalysts are preferred over amorphous catalysts because of their much-improved selectivity to desired products. Zeolites are the most commonly used molecular sieves in FCC processes. Preferably, the first catalyst component comprises a large pore zeolite, such as a Y-type zeolite, an active alumina material, a binder material, comprising either silica or alumina and an inert filler such as kaolin.

The zeolitic molecular sieves appropriate for the first catalyst component should have a large average pore size. Typically, molecular sieves with a large pore size have pores with openings of greater than 0.7 nm in effective diameter defined by greater than 10 and typically 12 membered rings. Pore Size Indices of large pores are above about 31. Suitable large pore zeolite components include synthetic zeolites such as X-type and Y-type zeolites, mordenite and faujasite. It has been found that Y zeolites with low rare earth content are preferred in the first catalyst component. Low rare earth content denotes less than or equal to about 1.0 wt % rare earth oxide on the zeolite portion of the catalyst. Octacat™ catalyst made by W. R. Grace & Co. is a suitable low rare earth Y-zeolite catalyst.

The second catalyst component comprises a catalyst containing, medium or smaller pore zeolite catalyst exemplified by ZSM-5, ZSM-11, ZSM-12, ZSM-23, ZSM-35, ZSM-38, ZSM-48, and other similar materials. U.S. Pat. No. 3,702,886 describes ZSM-5. Other suitable medium or smaller pore zeolites include ferrierite, erionite, and ST-5, developed by Petroleos de Venezuela, S. A. The second catalyst component preferably disperses the medium or smaller pore zeolite on a matrix comprising a binder material such as silica or alumina and an inert filer material such as kaolin. The second component may also comprise some other active material such as Beta zeolite. These catalyst compositions have a crystalline zeolite content of 10-25 wt % or more and a matrix material content of 75-90 wt %. Catalysts containing 25 wt % crystalline zeolite material are preferred. Catalysts with greater crystalline zeolite content may be used, provided they have satisfactory attrition resistance. Medium and smaller pore zeolites are characterized by having an effective pore opening diameter of less than or equal to 0.7 nm, rings of 10 or fewer members and a Pore Size Index of less than 31.

The total catalyst composition should contain 1-10 wt % of a medium to small pore zeolite with greater than or equal to 1.75 wt % being preferred. When the second catalyst component contains 25 wt % crystalline zeolite, the composition contains 4-40 wt % of the second catalyst component with a preferred content of greater than or equal to 7 wt %. ZSM-5 and ST-5 type zeolites are particularly preferred since their high coke resistivity will tend to preserve active cracking sites as the catalyst composition makes multiple passes through the riser, thereby maintaining overall activity. The first catalyst component will comprise the balance of the catalyst composition. The relative proportions of the first and second components in the catalyst composition will not substantially vary throughout the FCC unit 14.

The high concentration of the medium or smaller pore zeolite in the second component of the catalyst composition improves selectivity to light olefins by further cracking the lighter naphtha range molecules. But at the same time, the resulting smaller concentration of the first catalyst component still exhibits sufficient activity to maintain conversion of the heavier feed molecules to a reasonably high level.

The relatively heavier feeds suitable for processing in accordance herewith include conventional FCC feedstocks or higher boiling or residual feeds. A common conventional feedstock is vacuum gas oil which is typically a hydrocarbon material prepared by vacuum fractionation of atmospheric residue and which has a broad boiling range of from 315-622° C. (600-1150° F.) and, more typically, which has a narrower boiling point range of from 343-551° C. (650-1025° F.). Heavy or residual feeds, i.e., hydrocarbon fractions boiling above 499° C. (930° F.), are also suitable. The fluidized catalytic cracking processing the invention is typically best suited for feedstocks that are heavier than naptha range hydrocarbons boiling above about 177° C. (350° F.).

The effluent or at least a selected portion thereof is passed from the fluidized reactor zone 14 through a line 16 into a hydrocarbon separation system 20, which may include a main column section 22 and a staged compression section 24. The main column section 22 may desirably include a main column separator and associated overhead receiver where the fluidized reactor zone effluent can be separated into desired fractions including a main column vapor stream that is passed through line 26 to the two stage compressor 24, and a main column liquid stream, which is passed through line 30 to the absorber 40. To facilitate illustration and discussion, other fraction lines such as including a heavy gasoline stream, a light cycle oil ("LCO") stream, a heavy cycle oil ("HCO") stream and a clarified oil ("CO") stream, for example, may not be shown or specifically described.

The main column vapor stream line 26 is introduced into the staged compression section 24. The staged compression section 24 results in the formation of a high pressure separator liquid stream in a line 32 and a high pressure separator vapor stream in a line 34. While the pressure of such high pressure liquid and high pressure vapor can vary, in practice such streams are typically at a pressure ranging from about 1375 kPag to about 2100 kPag (about 200 psig to about 300 psig). The compression section 24 may also result in the formation of a stream of spill back materials largely composed of heavier hydrocarbon materials and such as can be returned to the main column section 22 via the line 35.

The high pressure separator liquid stream 32 includes $C_3+$ hydrocarbons and is substantially free of carbon dioxide and hydrogen sulfide. The high pressure separator vapor stream 34 includes $C_3-$ hydrocarbons and typically includes some carbon dioxide and hydrogen sulfide.

The separator vapor stream line 34 is introduced into an absorption zone 36, which includes the primary absorber 40, where the separator vapor stream 34 is contacted with a debutanized gasoline material provided by the line 42 and the main column overhead liquid stream 30 to absorb $C_3+$ materials and separate $C_2$ and lower boiling fractions from the separator vapor stream. In general, the absorption zone 36 includes the primary absorber 40 that suitably includes a plurality of stages with at least one and preferably two or more intercoolers interspaced therebetween to assist in achieving desired absorption. In practice, such a primary absorber 40 includes about five absorber stages between each pair of intercoolers. The primary absorber 40 may include at least about 15 to 25 ideal stages with 2 to 4 intercoolers appropriately spaced therebetween.

$C_3+$ hydrocarbons absorbed in or by the debutanized gasoline stream 42 and main column liquid stream 30 in the absorber 40 can be passed via the line 43 back to the two-stage compressor 24 for further processing. The off gas from the primary absorber 40 passes via a line 44 to a secondary or sponge absorber 46. The secondary absorber 46 contacts the off gas with light cycle oil from a line 50. Light cycle oil absorbs most of the remaining $C_4$ and higher hydrocarbons and returns to the main fractionators via a line 52. A stream of $C_2-$ hydrocarbons is withdrawn as off gas from the secondary or sponge absorber 46 in the line 54 for further treatment as later described herein.

The high pressure liquid stream 32 from the compressor 24 is passed through to the stripper 62 which removes most of the $C_2$ and lighter gases through the line 64 and passes them back to the compressor 24. In practice, the stripper 62 can be operated at a pressure ranging from about 1375 kPag to about 2100 kPag (about 200 psig to about 300 psig) with a $C_2/C_3$ molar ratio in the stripper bottoms of less than 0.001 and preferably with a $C_2/C_3$ molar ratio in the stripper bottoms of less than about 0.0002 to about 0.0004.

As discussed in greater detail below, the reboiler heat exchanger 63 may be heated by the alkylation reactor 164 shown in FIGS. 2 and 3. Specifically, one or more intercoolers 63a, 63b (FIGS. 2-3) may be combined with the reboiler heat exchanger 63 (FIG. 1) associated with the stripper 62.

As shown, the $C_2$ and lighter gases in the line 64 are combined in the compressor 24 with the main column vapor stream 26 to form with high pressure separator vapor stream 34 that is fed into the primary absorber 40. The stripper 62 supplies a liquid $C_3+$ stream 66 to the debutanizer 70. A suitable debutanizer 70 includes a condenser (not shown) that desirably operates at a pressure ranging from about 965 kPag to about 1105 kPag (about 140 psig to about 160 psig), with no more than about 5 mol % $C_5$ hydrocarbons in the overhead and no more than about 5 mol % $C_4$ hydrocarbons in the bottoms. More preferably, the relative amount of $C_5$ hydrocarbons in the overhead is less than about 1-3 mol % and the relative amount of $C_4$ hydrocarbons in the bottoms is less than about 1-3 mol %.

A stream of $C_3$ and $C_4$ hydrocarbons from the debutanizer 70 is taken as overhead through the line 72 for further treatment as described below and the bottoms stream 76 from the debutanizer 70 comprises gasoline, part of which forms the stream 42 which is fed to the top of the primary absorber 40 where it serves as the primary first absorption solvent. Another portion of the stream of debutanized gasoline is passed in the line 77 to a naphtha splitter (not shown), which may be a dividing wall separation column.

The $C_2-$ hydrocarbon stream 54 withdrawn from the secondary or sponge absorber 46 is passed through a further compression section 90 to form a compressed vapor stream 92 that is passed into a compression or discharge vessel 94. The discharge vessel 94 forms a liquid knockout stream generally composed of heavy components (e.g., $C_3+$ hydrocarbons that liquefy in the discharge vessel 94) and are withdrawn in the line 96. The discharge vessel 94 also forms an overhead vapor stream 100, primarily comprising $C_2-$ hydrocarbons, with typically no more than trace amounts (e.g., less than 1 wt %) of $C_3+$ hydrocarbons.

The overhead stream 100 is passed to an amine treatment section 102 to remove $CO_2$ and $H_2S$. The utilization of amine treatment system 102 for carbon dioxide and/or hydrogen sulfide removal is well known in the art. Conventional such amine treatment systems typically employ an amine solvent such as methyl diethanol amine (MDEA) to absorb or otherwise separate $CO_2$ and $H_2S$ from hydrocarbon stream materials. A stripper or regenerator is typically subsequently used to strip the absorbed $CO_2$ and $H_2S$ from the amine solvent, permitting the reuse of the amine solvent.

While such amine treatment has proven generally effective for removal of carbon dioxide from various hydrocarbon-containing streams, the application of such amine treatment to ethylene-rich hydrocarbon and carbon dioxide-containing streams, such as being processed at this point of the subject system, may experience some undesired complications as some of the olefin material may be co-absorbed with the $CO_2$ and $H_2S$ in or by the amine solvent. Such co-absorption of olefin material undesirably reduces the amounts of light olefins available for recovery from such processing. Moreover, during such subsequent stripper processing of the amine solvent, the presence of such olefin materials can lead to polymerization. Such polymerization can lead to degradation of the amine solvent and require expensive off-site reclamation processing.

In view thereof, it may be desirable to utilize an amine treatment system such as includes or incorporates a pre-stripper interposed between the amine system absorber and the amine system stripper/regenerator. Such an interposed pre-stripper, can desirably serve to separate hydrocarbon materials, including light olefins such as ethylene, from the carbon dioxide and amine solvent prior to subsequent processing through the regenerator/stripper. A $CO_2/H_2S$ outlet is shown at 103.

A stream 104 containing $C_2-$ hydrocarbons substantially free of carbon dioxide and hydrogen sulfide passes to a dryer section 106 with a water outlet line 107. A stream containing dried $C_2-$ hydrocarbons substantially free of carbon dioxide and hydrogen sulfide passes via a line 108 to an acetylene conversion section or unit 110. As is known in the art, acetylene conversion sections or units are effective to convert acetylene to form ethylene. Thus, an additionally ethylene-enriched process stream 112 is withdrawn from the acetylene conversion section or unit 110 and passed to the optional dryer 114 or to the $CO_2$, carbonyl sulfide ("COS"), arsine and/or phosphine treater 116 as is known in the art to effect removal of $CO_2$, COS, arsine and/or phosphine.

Water is withdrawn from the dryer 114 through the line 117. $CO_2$, COS, Arsine and/or Phosphine are withdrawn through the line 118, and the treated stream 120 is introduced into a demethanizer 122. A suitable demethanizer 122 may include a condenser (not specifically shown) that desirably operates at a temperature of no greater than about −90° C. (−130° F.), more preferably operates at a temperature ranging from about −90° C. to about −102° C., preferably about −96° C. (−130° to about −150° F., preferably at about −140° F.). In addition, the demethanizer 122 may operate with a methane to ethylene molar ratio in the bottoms of no greater than about 0.0005 and, more preferably at a methane to ethylene molar ratio in the bottoms of no greater than about 0.0003 to about 0.0002.

The overhead stream 124 of methane and hydrogen gas from the demethanizer 122 may be used as a fuel or, if desired, taken for further processing or treatment such as to a pressure swing absorption unit (not shown) for $H_2$ recovery. The demethanizer outlet stream 126 is passed directly to an ethyl benzene unit 10b of FIG. 2 or 10c of FIG. 3 without the need for heating or a splitter to separate the ethane from the ethylene. By avoiding the use of a $C_2/C_2$=splitter, which would operate at a pressure ranging from about 1930 kPag to about 2105 kPag (about 280 psig to about 305 psig), substantial savings in terms of operating coast and capital costs are achieved.

Still referring to FIG. 1, the stream 72 containing $C_3$ and $C_4$ hydrocarbons taken overhead from the debutanizer 70 may contain some significant relative amounts of hydrogen sulfide and is therefore preferably passed to a hydrogen sulfide removal treatment unit 128, such as an amine treatment section, where hydrogen sulfide is removed through the line 129 and the treated stream 130 is passed to an optional extraction unit 132 to catalytically oxidize mercaptans present to disulfides via a caustic wash, which are removed through the line 134.

The resulting stream 136 is passed to the $C_3/C_4$ splitter 138. A suitable $C_3/C_4$ splitter includes a condenser (not specifically shown) that desirably operates at a pressure ranging from about 1650 kPag to about 1800 kPag (about 240 psig to about 260 psig), preferably at a pressure of about 1724 kPa (about 250 psig) and desirably operates such that there is no more than about 5 mol % $C_4$s in the overhead product stream, preferably less than about 1 mol % $C_4$s in the overhead product stream and no more than about 5 mol % $C_3$s in the bottoms stream, preferably less than about 1 mol % $C_3$s in the bottoms stream.

The $C_3/C_4$ splitter 138 forms a bottoms stream 140 of $C_4+$ hydrocarbons for use as either for product recovery or further desired processing, as is known in the art. The $C_3/C_4$ splitter 138 also forms a stream 142 composed primarily of $C_3$ hydrocarbons which is passed to a propylene/propane splitter 144. A suitable such propane/propylene splitter 144 may operate such that at least 98 wt % and, preferably, at least about 99 wt % of the propylene is recovered in the overhead stream and the propylene in the overhead stream is at least about 99.5% pure.

The propylene/propane splitter 144 forms a propylene stream 146 and a propane stream 148. The propylene stream 146 may be passed to dryer 150 for the removal of water through the line 152 before being passed on to a regenerative COS treater 154 to remove COS through the line 156 before being passed through the arsine and/or phosphine treater 158 to effect removal of trace amounts of arsine and/or phosphine through the line 160 and producing an propylene product stream 162.

Turning to FIG. 2, the combined ethane/ethylene stream 126 is introduced at various stages 165a-165f of the alkylation reactor 164, without pre-heating and without separating the ethane, where the ethylene reacts catalytically with benzene provided in the form of fresh benzene through the line 166 and recycled benzene through the line 168. Because ethane is essentially inert to the ethyl benzene process system 170, the need for an upstream ethane/ethylene splitter is not required. Further, pre-heating the cool stream 126 from the demethanizer 122 is not required as the low temperatures have been surprisingly found to improve selectivity in the alkylation reactor 164 as explained below. As the material in the combined ethane/ethylene stream 126 is liquid, it may be delivered at pressures ranging from about 2900 to about 4000 kPa (~421 to ~580 psi) using a conventional pump 125 instead of a more expensive compressor that would be required to deliver polymer grade ethylene gas to the alkylation reactor 164.

Ethylene in the stream 126 reacts with the benzene in the alkylation reactor 164 to produce a combined product stream 172 that will include ethyl benzene, diethyl benzene (DEB), triethyl benzene (TEB) and unreacted ethane, ethylene and benzene.

The combined alkylation product stream 172 is passed to a benzene column 174 where it is combined with a transalkylation product stream 176 from the transalkylation reactor 178. The transalkylation reactor 178 converts the polyethyl benzenes (PEBs) such as DEB and TEB to EB and DEB respectively. Hence, the feed for the transalkylation reactor 178 may include a PEB stream 182 from the PEB column 180 coupled with benzene from the line 168a taken from the feed line 168 to the alkylation reactor 164. The combined benzene/PEB stream 184 enters the transalkylation reactor 178 after being heated by the boiler or heater 186. The transalkylation product stream 176 will include lower amounts of PEBs.

The benzene column 174 removes benzene and lighter components through the overhead stream 188 which passes through condenser 190 and into the receiver 192. Condensed benzene is recycled through the lines 168 and 168a to the alkylation reactor 164 and transalkylation reactor 178 respectively. The vapor stream 194 from the condenser 192 is passed to the lights removal column 196 where off gases are removed through the line 198 and cooling water is provided through the line 200. Heavier components are drawn out the bottom of the column 196 through the line 202 before passing into a collector 204 and through the line 206 to be recycled back to the receiver 192.

The bottoms stream 208 from the benzene column 174 contains ethyl benzene and heavier materials and is passed on to the ethyl benzene column 210. The lighter ethyl benzene passes as overhead through the line 212, condenser 214, and a receiver 216 to the ethyl benzene product outlet 218. The bottoms stream 220 from the ethyl benzene column 210 is passed on to the PEB column 180 where PEBs are separated from heavier components to produce a PEB product stream 220 and bottoms stream 222 which is essentially a flux oil discharge stream. The PEB stream 220 passes through the condenser 224 and receiver 226 before being recycled through the line 184 to the transalkylation reactor 178.

The intercoolers 63a, 63b in the alkylation section 164 typically require a cooling water utility. In accordance with this disclosure, integrating the alkylation intercoolers 63a, 63b (FIGS. 2-3) with the $C_2$- stripper 62 saves about 24 MM kcal/hr of additional heating by LP steam which would be required by the reboiler 63 (FIG. 1). All of the heat for the reboiler 63 can be provided by the two intercoolers 63a, 63b, each of which typically require about −16.5 MM kcal/hr for the case described here. Additional cooling water duty will be required to remove the additional 9 MM kcal/hr of heat in the intercoolers 63a, 63b, but overall the process is more efficient by reducing the steam requirement for the stripper 62, as well as much of the cooling water requirement in the alkylation section 164.

Injecting the cold, liquid combined ethane/ethylene steam 136 provides a direct heat exchange benefit in the alkylation reactor 164. First, the hotter catalyst beds 165b, 165d and 165f have a lower inlet temperature. This may result in better EB selectivity as some EB alkylation catalysts (such as UZM-8) have a slightly better EB selectivity at lower temperatures. Further, the lower inlet temperatures to the alkylation reactor 164 provide reduced formation of heavies, such as diphenyethane (DPE) and ethyldiphenylethane (EDPE). The outlet temperature of the hot catalyst beds 165b, 165d and 165f is also somewhat lower. Therefore, the two intercoolers 63a, 63b have a smaller duty requirement, and even with the transfer of heat to the splitter column 62, a savings results in terms of equipment cost (smaller heat exchanger area requirement), and utilities as cooling water costs are reduced. A small portion of this advantage is offset by the need to heat the recycle benzene in the line 168 to a slightly hotter temperature in order to achieve the desired alkylation inlet temperature.

An overall summary of the disclosed process and integrated is shown in following tables with the date in the middle column being generated using a cool liquid combined ethane/ethylene stream and the data in right column using a conventional gaseous ethylene feed.

TABLE 1

| C2 Feed Properties | Mixed C2 (Ethane/Ethylene) | Polymer Grade Ethylene (Prior Art) |
|---|---|---|
| Ethylene Content (wt %) | 87% | 99.5% |
| Temperature, ° C. | 12.2 | 89.5 |
| Pressure (kPa) | 4,520 | 4,520 |
| Phase | Liquid | Gas |
| Ethylene Process Rate kg/hr | 65,435 | 65,434 |

TABLE 2

| Alkylation Chemistry | Mixed C2 (Ethane/Ethylene) | Polymer Grade Ethylene (Prior Art) |
|---|---|---|
| Ethyl Benzene Selectivity | 87.87% | 87.69% |
| Diethyl Benzene Selectivity | 11.34% | 11.45% |
| Triethyl Benzene Selectivity | 0.70% | 0.75% |
| Others | 0.09% | 0.11% |
| Total | 100.00% | 100.00% |

TABLE 3

| Heavy Byproducts | Mixed C2 (Ethane/Ethylene) | Polymer Grade Ethylene (Prior Art) |
|---|---|---|
| Diphenylethane | 0.045% | 0.052% |
| Ethyldiphenylethane | 0.015% | 0.018% |

TABLE 4

| | Alkylation Reactor Inlet Temperatures (° C.) for Six Bed Reactor | |
|---|---|---|
| | Mixed C2 (Ethane/Ethylene) | Polymer Grade Ethylene (Prior Art) |
| Bed 1 (Bottom; see bed 165a in FIG. 2) In | 200.00 | 200.00 |
| Bed 1 Out | 228.32 | 228.40 |
| Bed 2 In | 222.24 | 227.13 |
| Bed 2 Out | 248.80 | 252.88 |
| Bed 3 In | 200.00 | 200.00 |
| Bed 3 Out | 227.51 | 227.73 |
| Bed 4 In | 222.01 | 226.50 |
| Bed 4 Out | 247.38 | 251.79 |
| Bed 5 In | 200.00 | 200.00 |
| Bed 5 Out | 226.69 | 227.06 |
| Bed 6 (Top) In | 221.17 | 225.81 |
| Bed 6 Out | 246.02 | 250.79 |

TABLE 5

| | Alkylation Intercooler Duties (MM kcal/hr) | |
|---|---|---|
| | Mixed C2 (Ethane/Ethylene) | Polymer Grade Ethylene (Prior Art) |
| Lower Intercooler (see intercooler 63b in FIG. 2) | −16.5 | −19.4 |
| Upper Intercooler (see intercooler 63a in FIG. 2) | −16.5 | −19.4 |
| Total | −33 | −38.8 |

One additional integration option is illustrated in FIG. 3 and involves eliminating the transalkylation section 178 and the polyethyl benzenes (PEB) column 180. The ethyl benzene (EB) column bottoms 220 is passed to the primary absorber 40 by combining the ethyl benzenes bottoms stream 220 with the debutanized gasoline recycle stream 42 (FIG. 1) to supplement some of the debutanized gasoline recycle, reducing the amount of recycle that is required. If all of the ethylene produced by the FCC process 10a is used in the EB process 10c, the EB column bottoms 220 would reduce the required debutanized gasoline recycle stream 42 by an amount ranging from about 5 to about 10%. The polyethyl benzenes including DEB and PEB would ultimately end up as a high octane component in the gasoline product stream 76. Because the EB column bottoms 220 contains a small fraction of heavy components (e.g., diphenylethane, ethyldiphenylethane) that may be slightly too heavy for the gasoline pool, another alternative shown in FIG. 3 is to send the EB column bottoms 220 to the FCC main column 22, where the heavier species in this stream would be removed in a heavier fraction such as the heavy naphtha draw. The lighter species in this stream will still act to reduce the required debutanized gasoline recycle stream 42, as they will exit in the unstabilized gasoline stream 76 that is recovered from the main column overhead stream 26.

Thus, improved processing schemes and arrangements are provided for obtaining ethylene and ethane via the catalytic cracking of a heavy hydrocarbon feedstock and converting the ethylene into ethyl benzene without separating the ethane from the feed stream. More particularly, processing schemes and arrangements are provided that advantageously eliminate any separation of ethylene from ethane produced by a FCC process prior to using the combined ethylene/ethane stream as a feed for an ethyl benzene process.

The disclosed processes and schemes may be practiced in the absence of any element, part, step, component, or ingredient which is not specifically disclosed herein.

The invention claimed is:

1. An integrated system for catalytically cracking a hydrocarbon feedstock, obtaining selected hydrocarbon fractions including a combined ethane/ethylene stream and reacting the ethylene of the combined ethane/ethylene stream with benzene to produce an ethyl benzene product stream, the integrated system comprising:
    a fluidized reactor zone wherein the hydrocarbon feedstock contacts a catalyst to produce a cracked effluent stream including ethane and ethylene,
    a separation zone for separating the cracked effluent stream into at least one separator liquid stream and a separator vapor stream, the at least one separator liquid stream comprising $C_3+$ hydrocarbons, the separator vapor stream comprising ethane and ethylene;
    one or more treatment zones to remove impurities from the separator vapor stream to provide a combined ethane/ethylene stream;
    a process line feeding the combined ethane/ethylene stream to an alkylation reactor of an alkylation zone for reacting at least some of the ethylene in the combined ethane/ethylene stream with benzene to form ethyl benzene;
    a stripper for stripping $C_2-$ hydrocarbon materials from the separator liquid stream to form a $C_3+$ process stream substantially free of $C_2-$ hydrocarbons; and
    at least one heat exchanger for transferring heat from the alkylation reactor to the stripper.

2. The integrated system of claim 1 wherein the combined ethane/ethylene stream is liquid and the process line further comprises a pump to pump the combined ethane/ethylene stream to the alkylation reactor.

3. The integrated system of claim 1 wherein the alkylation zone comprises an ethyl benzene column to separate an ethyl benzene stream from a polyethyl benzenes stream, and wherein
    the polyethyl benzenes stream is in communication with the absorption zone for use as a solvent in an absorber.

* * * * *